(12) United States Patent
Lanzani

(10) Patent No.: US 8,776,582 B2
(45) Date of Patent: Jul. 15, 2014

(54) SENSOR DEVICE FOR MEASURING THE FLOW AND/OR THE LEVEL OF A FLUID OR OF A SUBSTANCE

(71) Applicant: Isanik S.R.L., Azzano Mella (IT)

(72) Inventor: Federico Lanzani, Azzano Mella (IT)

(73) Assignee: Isanik S.R.L., Azzano Mella (Brescia) (IT)

( * ) Notice: Subject to any disclaimer, the term of this patent is extended or adjusted under 35 U.S.C. 154(b) by 0 days.

(21) Appl. No.: 13/765,296

(22) Filed: Feb. 12, 2013

(65) Prior Publication Data

US 2013/0192352 A1   Aug. 1, 2013

Related U.S. Application Data

(63) Continuation-in-part of application No. PCT/IT2011/000296, filed on Aug. 12, 2011.

(30) Foreign Application Priority Data

Aug. 13, 2010  (IT) .............................. MI2010A1548

(51) Int. Cl.
*G01N 25/00* (2006.01)

(52) U.S. Cl.
USPC ...................................... 73/61.76; 73/290 R

(58) Field of Classification Search
USPC ........................................... 73/61.76, 290 R
See application file for complete search history.

(56) References Cited

U.S. PATENT DOCUMENTS

| 4,553,852 | A | * | 11/1985 | Derderian et al. ................. 374/1 |
| 6,440,129 | B1 | * | 8/2002 | Simpson .......................... 606/42 |
| 6,582,425 | B2 | * | 6/2003 | Simpson .......................... 606/32 |
| 2005/0109103 | A1 | | 5/2005 | Zimmermann |
| 2010/0319436 | A1 | * | 12/2010 | Sun et al. ...................... 73/61.46 |

FOREIGN PATENT DOCUMENTS

| DE | 202006003595 U1 | 5/2006 |
| EP | 1705463 A1 | 9/2006 |
| EP | 1821080 A1 | 8/2007 |
| FR | 2846091 A1 | 4/2004 |

OTHER PUBLICATIONS

PCT International Search Report / PCT/IT2011/000296 Mailed Feb. 11, 2011.

* cited by examiner

*Primary Examiner* — Hezron E Williams
*Assistant Examiner* — Rodney T Frank
(74) *Attorney, Agent, or Firm* — Novak Druce Connolly Bove + Quigg LLP

(57) ABSTRACT

A sensor device and a related method for measuring the flow of a fluid and/or for detecting the presence of a substance have such respective structural and functional features as to allow reliable measurements at very reduced costs. The sensor device includes at least a temperature difference sensor based on the Seebeck thermoelectric effect and integrated in a sensor device support, together with a heating element also integrated in this support. A method for measuring the flow of a fluid and/or the presence or the level of a substance uses the sensor device.

14 Claims, 10 Drawing Sheets

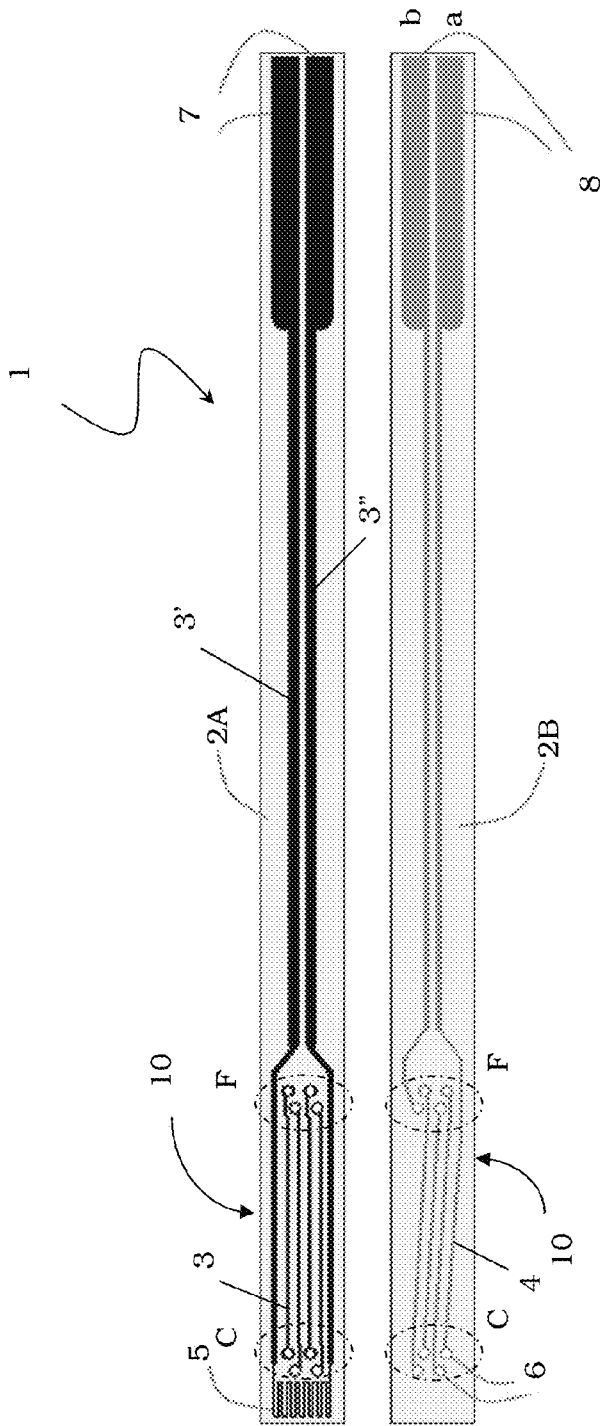
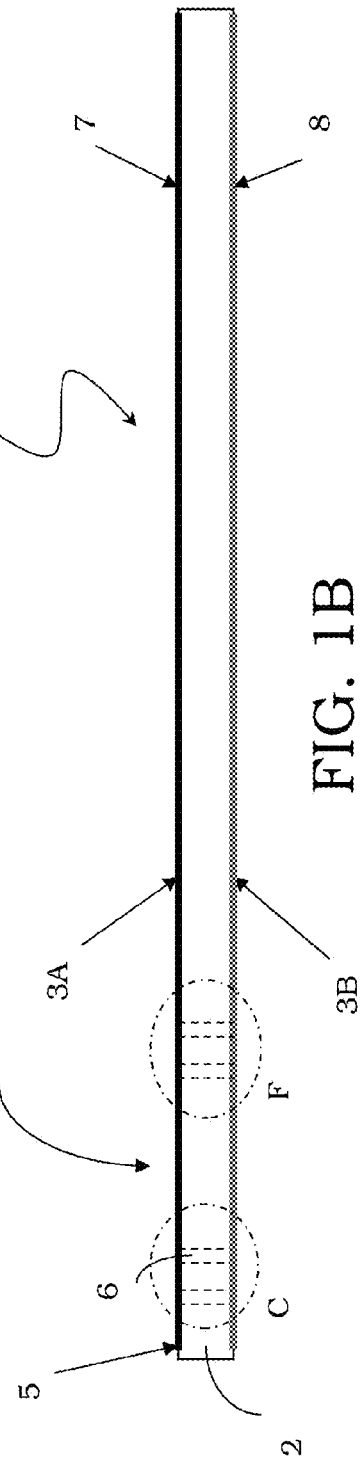
FIG. 1A
FIG. 1B

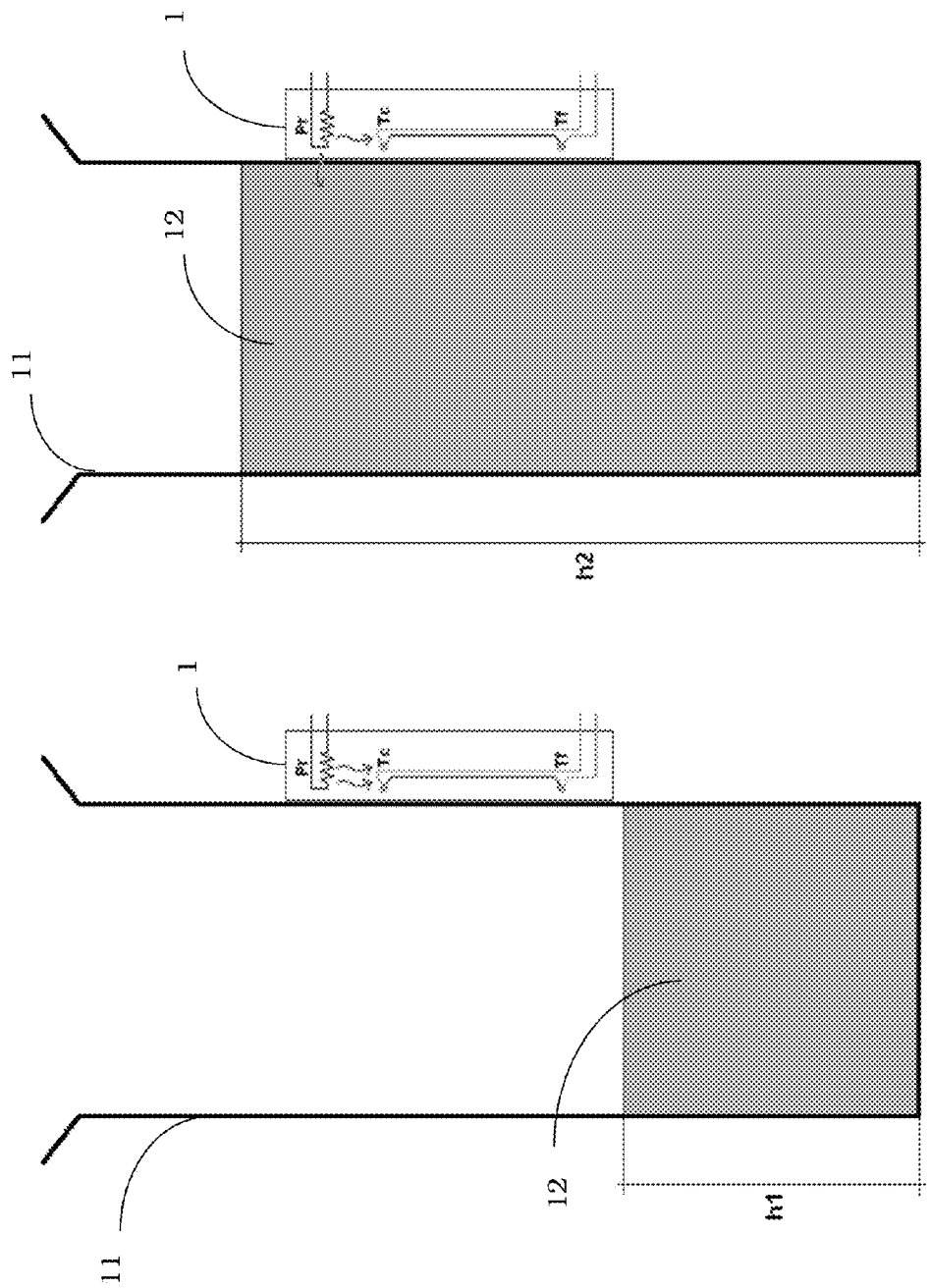

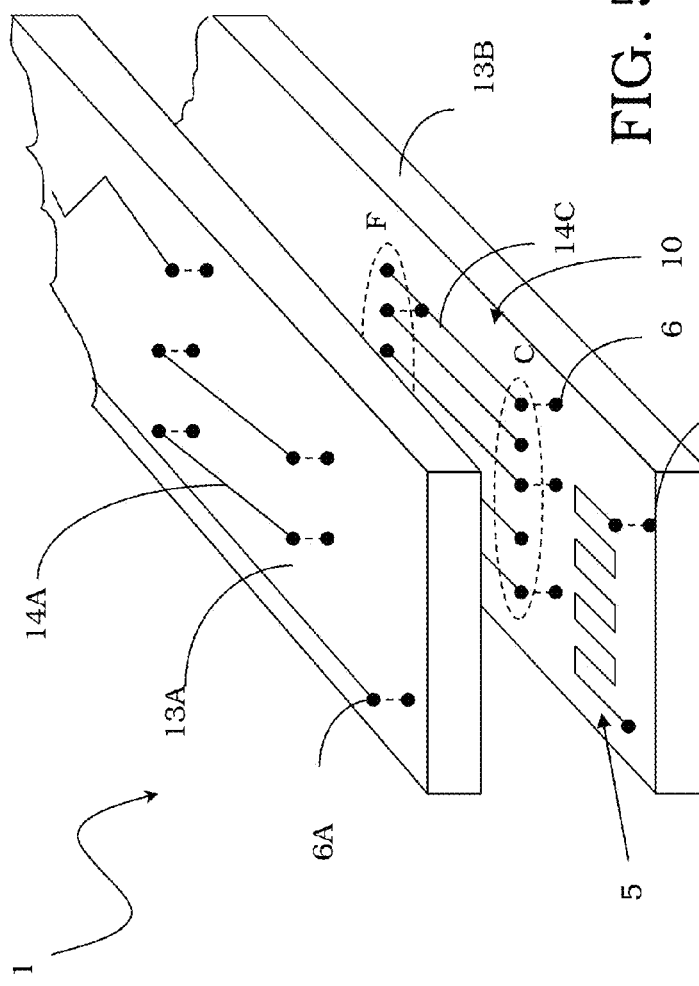
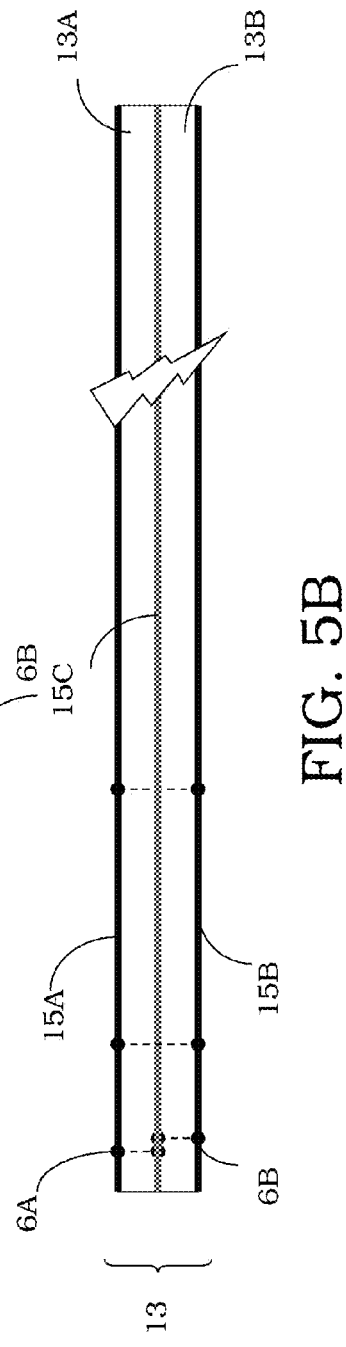

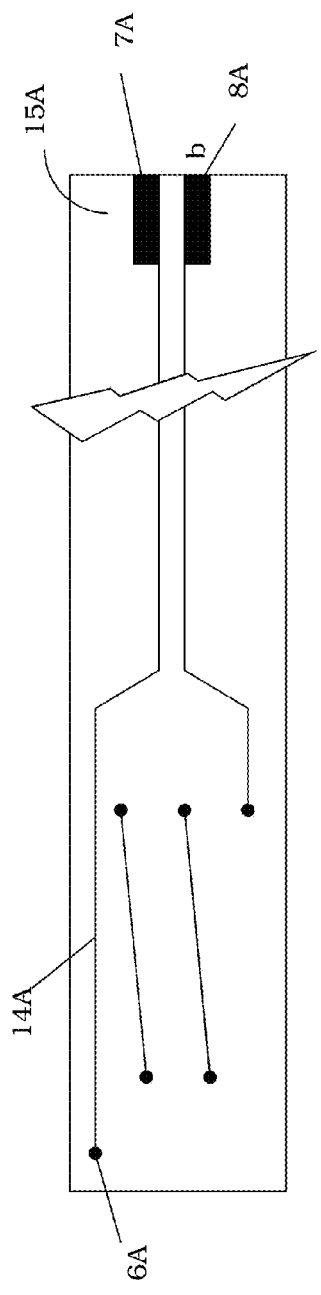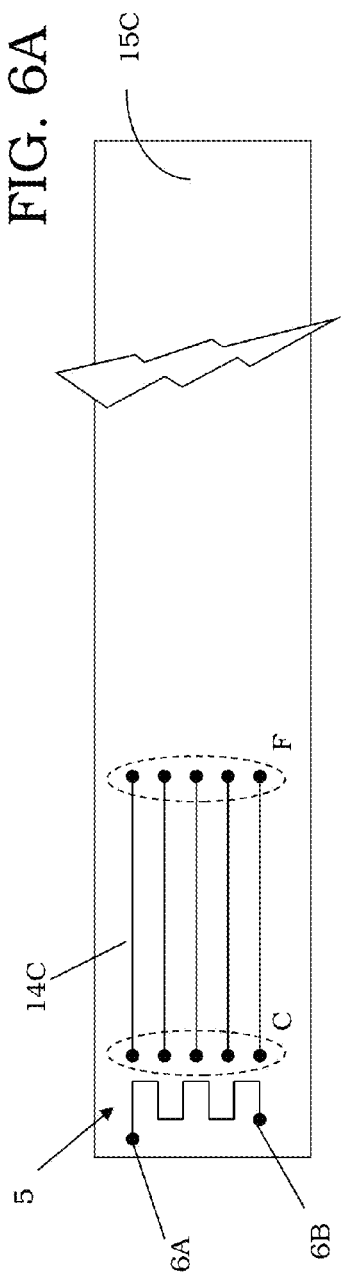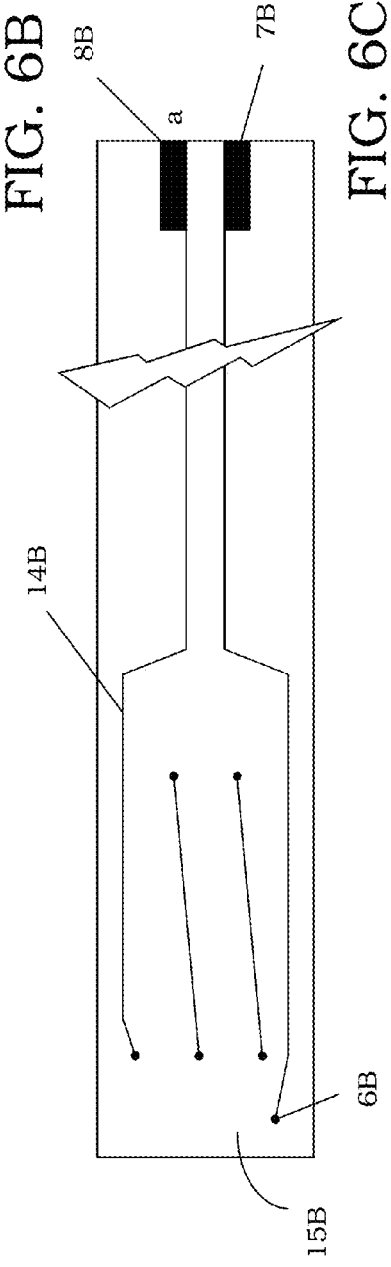

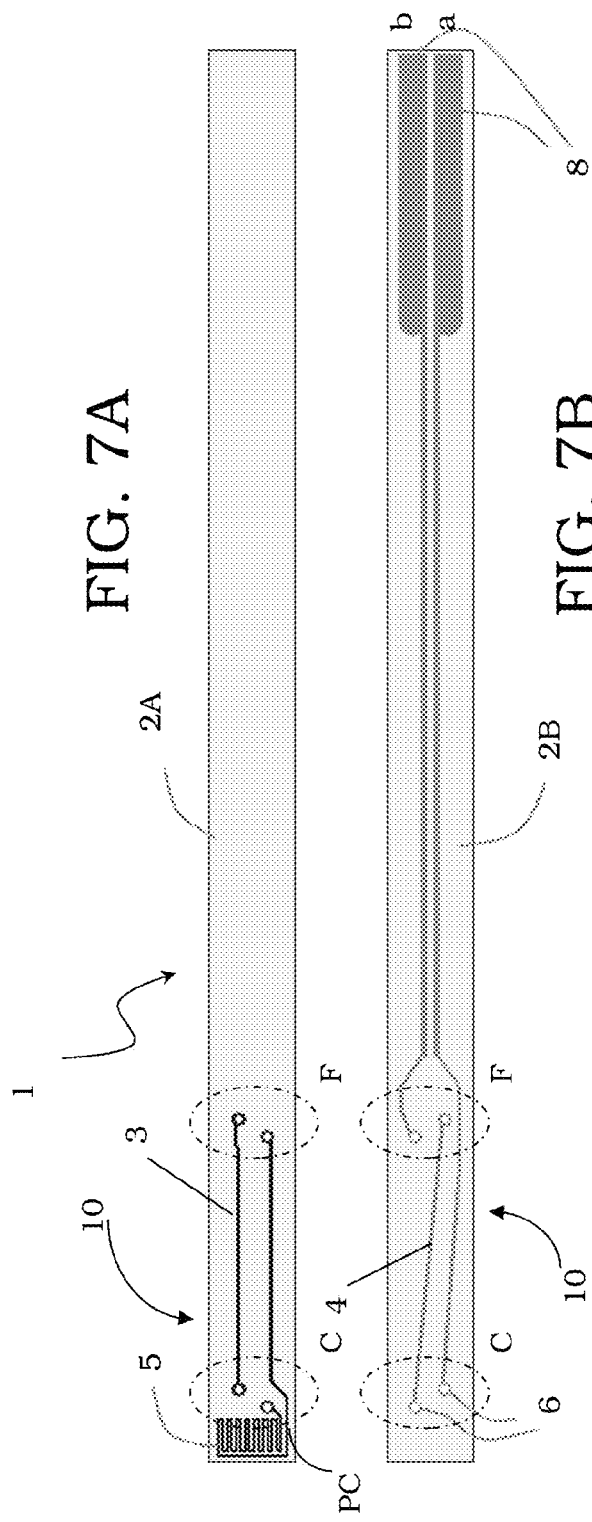
FIG. 7A
FIG. 7B
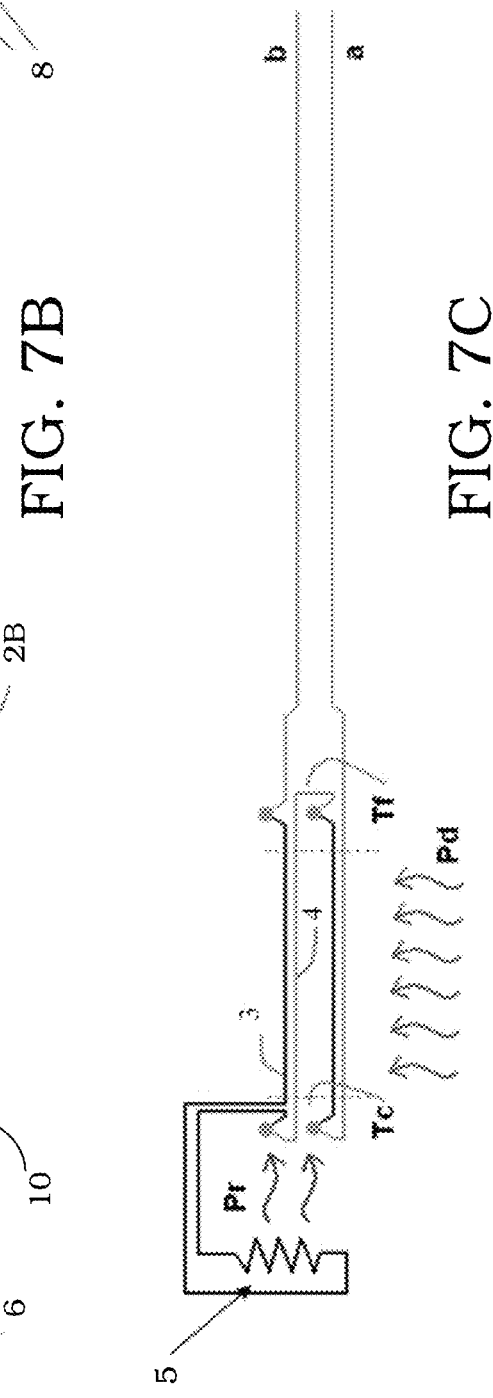
FIG. 7C

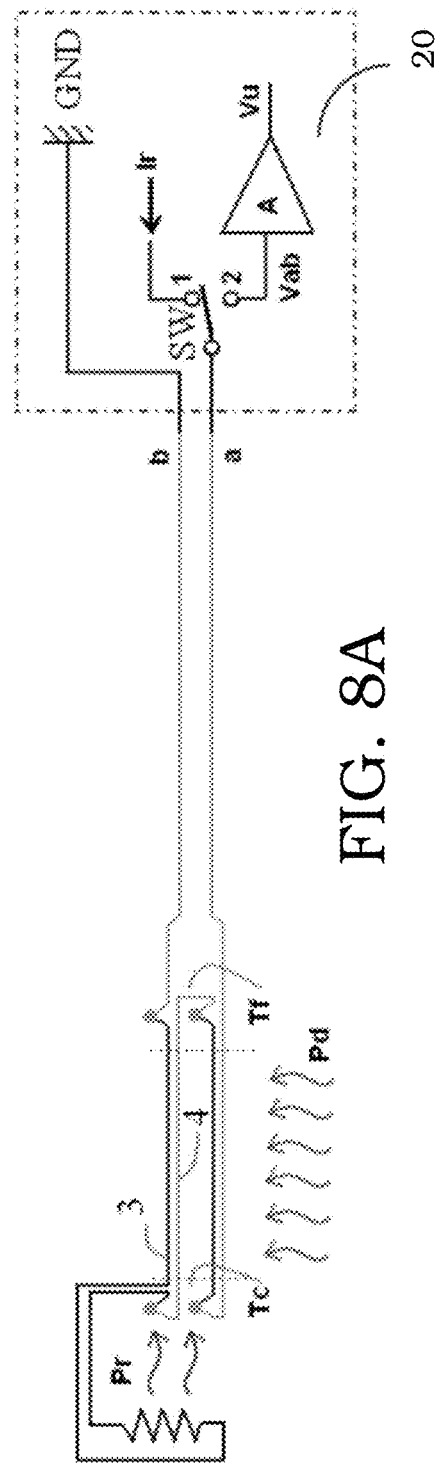
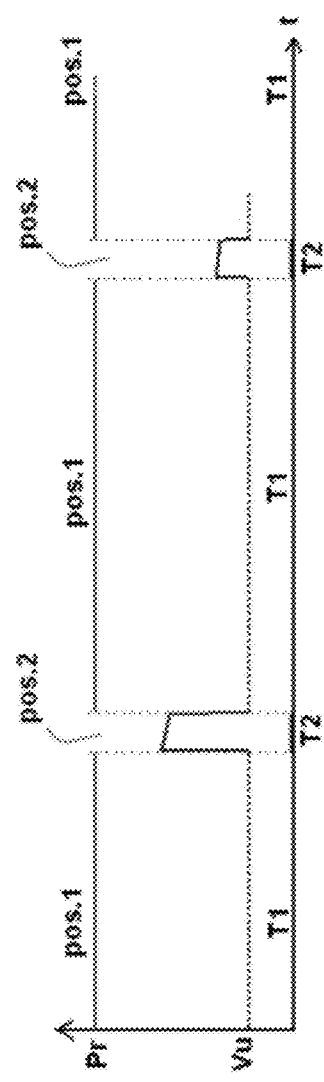
FIG. 8A
FIG. 8B

SENSOR DEVICE FOR MEASURING THE FLOW AND/OR THE LEVEL OF A FLUID OR OF A SUBSTANCE

CROSS-REFERENCE TO RELATED APPLICATIONS

This continuation-in-part application claims priority to International Application No. PCT/IT2011/000296 entitled "SENSOR DEVICE FOR MEASURING THE FLOW AND/OR THE LEVEL OF A FLUID OR OF A SUBSTANCE", filed Aug. 12, 2011, which claims priority to Italian Patent Application No. MI2010A 001548 filed on Aug. 13, 2010, which are hereby incorporated by reference in their entirety, for all purposes, herein.

FIELD OF THE INVENTION

In its broadest aspect, the present disclosure concerns a sensor device for measuring the flow of a fluid and, particularly, also for detecting the presence or the level of thick fluids or liquids or also of solid substances in the form of powders or small-sized granules.

More specifically, an embodiment of the invention concerns a sensor device of the above type and comprising a temperature difference sensor made by at least a thermocouple.

Another embodiment of the invention concerns the manufacturing of a family of sensors for measuring even the mere movement of fluids and/or for detecting the presence of liquids or even of solids and the following description is made with reference to this field of application for simplicity of exposition only.

BACKGROUND OF THE INVENTION

As it is well known to those skilled in the art, measuring of the flow of a fluid through temperature can be performed by exploiting two physical principles: the dissipative thermodynamic principle and the calorimetric principle.

The dissipative thermodynamic principle is based in particular on the difference between the fluid temperature and that of a body immersed therein, being heated with a constant, or anyway known, quantity of energy. This difference only depends on the heat exchange conditions between the body and the fluid, and it is thus functionally linked to the fluid speed as well as to its density.

The calorimetric principle is based instead on the temperature difference setting up in a fluid flow between the upstream and downstream of a heating region against the application of a known quantity of energy. The applicability of this principle requires the thermal uniformity of the fluid being measured.

Prior art already provides some solutions applying the dissipative thermodynamic principle to the measuring of a fluid motion.

There are in fact some devices essentially based on two resistive sensors, one of which is heated and the other is used to sense the fluid temperature, such as for example those described in the Application Note No. AN9801 by Farruggia et al.

However, these known devices have some drawbacks in terms of cost and measurement reliability. Moreover, known devices are often affected by measuring offsets and they require heavy and delicate calibration interventions. Another drawback is the difficulty in miniaturizing them, thereby they have a considerable size and dimensions.

These acknowledged drawbacks actually limit the possibility to widen the field of application of sensors being manufactured by exploiting the thermodynamic principle according to the prior art.

Prior art also provides some solutions applying the calorimetric principle to the measuring of a fluid motion.

For example, Patent GB1116178 describes a device for measuring the flow of a fluid, comprising three tubular sections made with two metals having different thermoelectric properties and arranged in series and alternated with each other. In this way, two junctions of a thermocouple have been formed, which are positioned at a predetermined distance from each other with an intermediate section associated with a heater and susceptible to be heated.

Although advantageous under several aspects, the device being provided by prior art is not without drawbacks due both to the complexity of manufacturing and coupling of the different parts and to the considerable total mass, which limits its application owing to the intrinsic thermal inertia.

Moreover, in operation, a considerable power is to be supplied to the heating element.

It should also be said that, when gaseous fluids are to be measured, the device sensitivity is considerably reduced because of the thermal masses involved to such an extent that it has proved to be inadequate for properly measuring low fluid speeds.

To obviate to this drawback, a sensor device exploiting the dissipative thermodynamic principle, comprising a thermocouple as a temperature sensor and heating means of a junction of said thermocouple, has been suggested in the European Patent Application no. EP1705463 in the name of Lanzani et al.

In particular, the sensor device being described in this application comprises the heating element on a support, some conductive tracks of metallic material being formed on the surface thereof in order to form thermocouple conductive tracks. The heating element can be made with an electrical resistor positioned on the support near the thermocouple.

Although advantageous under several aspects, also this known solution is not without drawbacks. In particular, the resistive-type heating element is an additional cost since it is manufactured separately and it is difficult to position and assemble, with considerable limits in terms of accuracy, giving rise to uncertainties and positioning and/or thermal contact tolerances which actually negatively influence the accuracy of the measuring being performed.

Moreover, the heating element, which is anyway added to the sensor device support, increases the mass and thus the thermal inertia near the hot junction, giving rise to a further disadvantage in terms of sensor response time. Finally, the sensor device final size should take into account the size of the heater as a separate element with related pads to be placed on the support of the sensor device itself.

Also known from the US Patent application published under No. US 2005/0109103 is a liquid level sensor using a plurality of thermocouple junctions. It should be remarked that, according to this document, heating elements are realized on the surface of the device, thus protruding from the same so increasing the global size of the device itself. Hence, the miniaturizing of this solution is limited and its cost quite high, the positioning of such heating elements also requiring ad hoc design and thus repetitivity problems.

SUMMARY OF THE INVENTION

An embodiment of the disclosure is directed to a sensor device and a related method for measuring the flow of a fluid and/or for detecting the presence of a substance, the device and the method having such respective structural and functional features as to allow reliable measurements at very reduced costs.

A further embodiment of the disclosure is a sensor device which is strong, reliable, economical, miniaturizable, accurate, fast and susceptible of being used in several applications.

The sensor device comprises at least a temperature difference sensor based on the Seebeck thermoelectric effect and integrated in a sensor device support, together with a heating element also integrated in this support.

In particular, the sensor device for measuring the flow of a fluid and/or the presence or the level of a substance comprises a support being equipped with a temperature difference sensor based on the Seebeck thermoelectric effect and being a multi-layer printed circuit board support which includes at least one first insulating support, a second insulating support, an inner conductive layer of a first conductive material separating the first and second insulating supports, the first and second insulating supports having their respective exposed surfaces coated with a first conductive layer of a second conductive material and with a second conductive layer of the second conductive material, first conductive tracks which are obtained in the first and second conductive layers, and second conductive tracks which are realized in the inner conductive layer, through and metalized holes being provided in the first and second support elements to connect the first conductive tracks with the second conductive tracks, thus creating at least one thermocouple of the sensor, a heating element being also associated to the sensor and being internally realized in the multi-layer printed circuit board support in the inner conductive layer of the first conductive material.

More particularly, according to an embodiment of the disclosure, the first and second insulating supports can be insulating supports made of a laminated material as used in the printed circuit board technology.

The first conductive material can be constantan and the second conductive material can be copper.

Moreover, according to an aspect of the disclosure, the heating element can be directly made of and embedded in the inner conductive layer using the printed circuit board technology.

According to another aspect of the disclosure, the sensor device can further comprise power connections to the heating element which are made in the first and second conductive layers, in the form of contact pads, and output terminals for transferring an output signal of the sensor device, which are realized in the first and second conductive layers, in the form of contact pads.

Moreover, the sensor device can comprise at least first and second metalized through holes which are made in the first and second insulating supports respectively, for connecting the heating element to respective conductors which are made in the first and second conductive layers, respectively, and to provide a power supply current to the heating element.

Moreover, the sensor device can further comprise respective output terminals which are made in the first and second conductive layers respectively, for the transmission of an output signal of the sensor.

The heating element can also be electrically connected to the at least one sensor thermocouple of the sensor, preferably to the hot junction of the at least one thermocouple.

The sensor device can further comprise SMT electronic components provided on at least one of its surfaces for realizing onboard electronics for signal amplification and conditioning.

Furthermore, the heating element can be realized close to the at least one thermocouple of the sensor, preferably to the hot junction of the at least one thermocouple.

The sensor device can further comprise a plurality of sensors arranged close to each other.

Finally, the above-described sensor device can be used as an external sensor being fixed in a stable manner to a container and/or to a pipe for measuring the flow of a fluid and/or the presence or the level of a substance in the container and/or pipe as well, by comprising a plurality of sensors arranged close to each other, as an external sensor being fixed in a stable manner to a container and/or to a pipe to detect in more locations the achievement of a certain level of a substance in the container and/or pipe, thus obtaining an almost continuous level measuring.

The disclosure is also directed toward a method for measuring the flow of a fluid and/or the presence or the level of a substance wherein it uses a sensor device made as above indicated and it comprises the steps of:

supplying with an electric current the heating element associated to the sensor of the sensor device during a first time interval;

interrupting the supplying step of the electric current for a second time interval, which is shorter than the first time interval and fixed so as the temperatures of the hot and cold junctions of the sensor are substantially unchanged during the second time interval; and detecting a voltage signal provided at the output of the sensor during the second time interval, the voltage signal provided at the output of the sensor being proportional to the difference of the temperatures of the hot and cold junctions of the sensor and thus allowing the measuring of the flow of a fluid and/or the presence or level of a substance.

The features and advantages of the sensor device according to the invention will be apparent from the following description of an embodiment given with reference to the attached drawings.

BRIEF DESCRIPTION OF THE DRAWINGS

FIGS. 1A and 1B schematically show a sensor device in respective plan and side views;

FIGS. 4A and 4B schematically show the application of the sensor device according to an embodiment of the invention for measuring a level of a substance in a container;

FIGS. 5A and 5B schematically show a sensor device made through a multi-layer printed circuit board according to an embodiment of the invention;

FIGS. 6A-6C show in greater detail the multi-layer printed circuit board of the sensor device of FIGS. 5A and 5B;

FIGS. 7A-7C schematically show an alternative embodiment of the sensor device in respective plan views and according to an electric functional equivalent circuit thereof respectively;

FIGS. 8A and 8B schematically show the functional equivalent circuit of the sensor device of FIGS. 7A-7B associated to a detection circuit according to an embodiment of the invention and a voltage signal as detected respectively;

DETAILED DESCRIPTION

Figure 2:
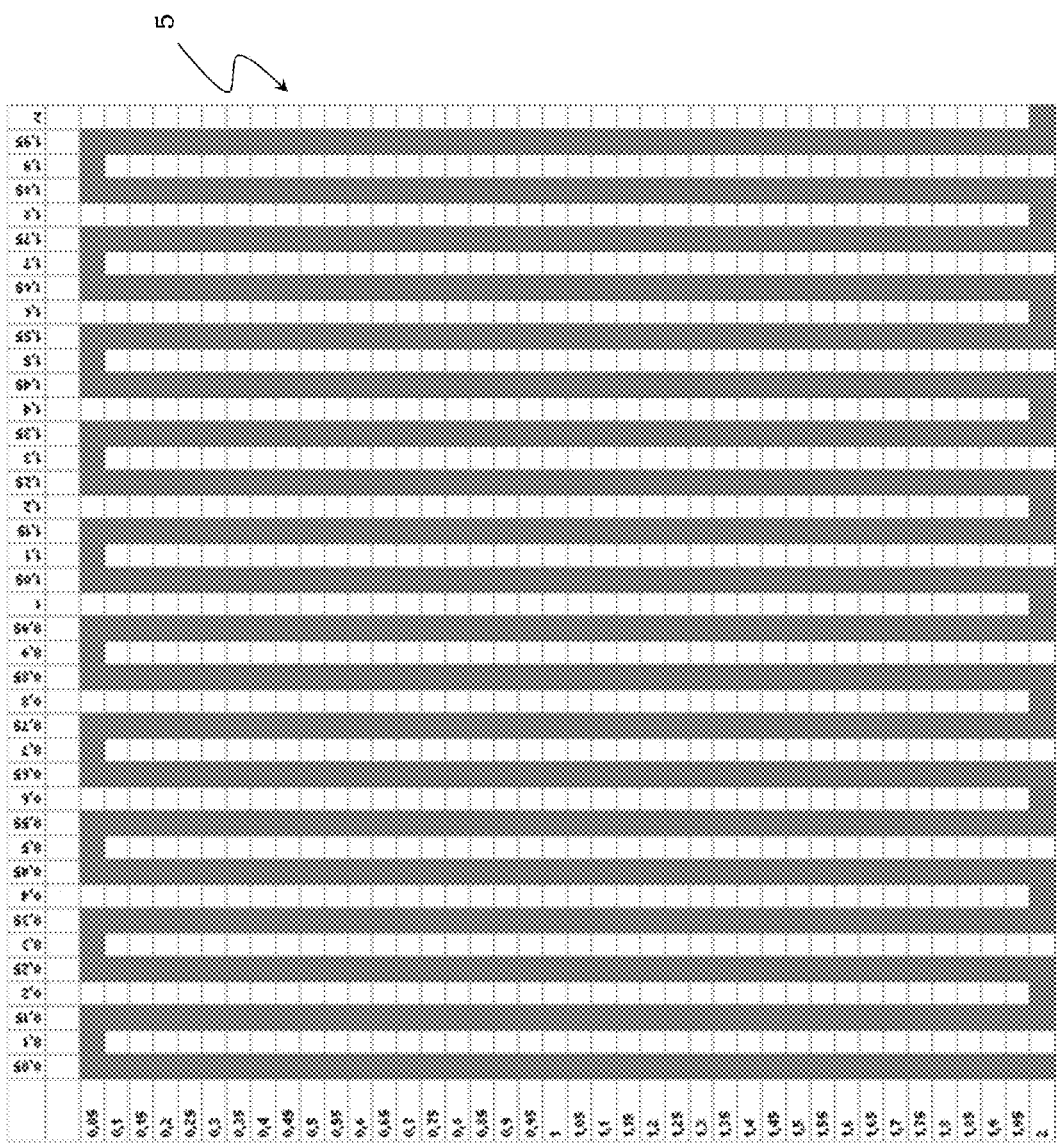
FIG. 2 schematically shows a heating element comprised in the sensor device of FIG. 1.

The following discussion is presented to enable a person skilled in the art to make and use the invention. Various modifications to the embodiments will be readily apparent to those skilled in the art, and the generic principles herein may be applied to other embodiments and applications without departing from the spirit and scope of the present invention. Thus, the present invention is not intended to be limited to the embodiments shown, but is to be accorded the widest scope consistent with the principles and features disclosed herein.

Referring to FIGS. 1A and 1B, a sensor device is globally and schematically shown with 1.

The sensor device 1 is in particular equipped with at least one temperature difference sensor 10 based on the Seebeck thermoelectric effect.

In particular, the sensor device 1, preferably made with the printed circuit board technology, comprises a support 2 in the form of a strip of electrically insulating material, being stiff or flexible, for example resin FR-4, Kapton®, PTFE, Polyimide, or even ceramic. The insulating laminated support 2 comprises at least a first side 2A coated with a first conductive layer 3A of a first metallic material, for example constantan, and a second side 2B coated with a second conductive layer 3B of a second metallic material, for example copper.

With regard to the use of constantan and copper it is explained that:
  constantan has a much higher resistivity than copper (more than 30 times higher), allowing heating elements to be made directly in the thin foil of the printed circuit board support (of course on the constantan side) with a small size, since for the same final resistive value the length of the copper conductive track would be more than 30 times higher;
  constantan associated to copper to form the thermocouple junctions has a thermoelectric effect with good features of sensitivity and linearity when the temperature changes; in the range of temperatures wherein the use of the sensor device is envisaged, the thermoelectric voltage generated by such a thermocouple for each degree of temperature difference between the hot and cold junctions amounts to about 40 microvolts (this feature is known as Seebeck coefficient).
  copper and constantan are metals having a good compatibility with each other and thus the junctions made between these elements have a good stability, even if they are made through the metalized holes (vias) wherein copper is deposited on the inner hole surface
  copper (and also constantan that comprises a high % of copper) are materials being used in the production and processing of printed circuit boards, making it possible to produce on a large scale and at low cost the sensor device 1 according to the invention.

All this does not obviously prevent from using other conductive materials which can form thermoelectric couples, provided that the above-indicated features are observed. In the following description reference will be made to a constantan layer and to a copper layer to indicate the first and second metallic materials of the first and second conductive layers for simplicity of exposition, meaning by these terms also equivalent conductive materials meeting the above-described requirements.

By applying the printed circuit board design and manufacturing techniques for electronic applications, in the first and second conductive layers, 3A and 3B, constantan and copper conductive tracks are obtained on the first and second sides, 2A and 2B, of the insulating laminated support 2, respectively indicated with 3 and 4, in particular a first series 3 of parallel tracks made of the first conductive material, i.e. of constantan, and a second series 4 of parallel tracks made of the second conductive material, i.e. of copper. Suitably, metalized holes (vias) 6 are made in the body of the insulating laminated support 2 to connect the conductive tracks 3 and 4 arranged on the opposite sides 2A and 2B of the insulating laminated support 2, thus forming at least one thermocouple. More particularly, in the example given by way of non-limiting example in FIGS. 1A and 1B, the sensor device 1 is suitably equipped with a circuit comprising four thermocouples being series-connected to each-other, globally called thermocouple circuit and always indicated with 10.

Furthermore, the sensor device 1 comprises a heating element 5, in the shape of a resistor made by thin constantan conductive tracks 3' and 3'' and positioned in correspondence with first junctions of the thermocouple circuit 10, indicated hereafter with hot junctions C, being opposite to second junctions, indicated with cold junctions F, completing the thermocouple circuit 10. These first and second junctions are made thanks to respective metalized holes 6 passing through the insulating laminated support 2. In this way, the hot junctions C, positioned near the constantan heating element 5 are subject to a rise in temperature with respect to cold junctions F, positioned far from this heating element 5.

This heating element 5 is obtained and embedded directly in the insulating laminated support 2 through the printed circuit board technology, particularly using constantan conductive tracks, with a clear reduction in the cost and size of the final sensor device 1.

It is worth underlying that, by making metalized connection holes 6 between the two opposite sides, side 2A comprising constantan conductive tracks and side 2B comprising copper conductive tracks, a thermocouple junction is obtained in correspondence with each hole in C and F regions, and thus a thermocouple sensor 10, which can thus be made thanks to the printed circuit board processing technology, i.e. with no need for further processing, and thus with a considerably reduced cost and a high reproducibility.

In its more general aspect, the present disclosure thus refers to a sensor device 1 for measuring the flow of a fluid and/or the presence or the level of a substance, of the type comprising a support, for example an insulating laminated support, equipped with a temperature difference sensor 10 based on the Seebeck thermoelectric effect.

The sensor 10 of FIGS. 1A and 1B is made in the insulating laminated support 2 and comprises a first conductive portion 3 made with a first conductive material, in particular constantan, on one side 2A of the insulating laminated support 2 and a second conductive portion 4, made with a second conductive material, in particular copper, on an opposite side 2B of the insulating laminated support 2. The sensor device 1 also comprises a third conductive portion 6 connecting the first and second conductive portions, 3 and 4, through the insulating laminated support 2.

Furthermore, the sensor 10 is associated to a heating element 5 which is included in turn in the insulating laminated support 2.

In particular, the heating element 5 can be made in the form of a coil-shaped constantan resistor, as schematically shown in FIG. 2.

Through the present printed circuit board manufacturing technologies, it is in fact possible to make constantan tracks with a width being also lower than 0.1 mm and to obtain the heating element 5 directly in the constantan side 2A. In the illustrative example of FIG. 2, in a region of 2×2 mm an overall length of about 40 mm of the constantan conductive track is obtained, arranging about twenty constantan tracks with a width of 50 microns (equal to 0.05 mm) to make this heating element 5 as a constantan resistor. In particular, starting from a constantan metal foil 2A with a thickness of 5 microns, a resistive value of 80 ohms for the heating element 5 is obtained, as pointed out from the following table:

TABLE 1

| CONSTANTAN | | Data | calculations |
|---|---|---|---|
| Resistivity | Ohm * mm$^2$/m | 0.5 | |
| Length | m | 0.04 | |
| Track width | mm | 0.05 | |
| Track thickness | microns | 5 | |
| Track section | mm$^2$ | | 0.00025 |
| Resistance | Ohm | | 80 |

The sensor device 1 further comprises power connections 7 to the heating element 5, made of constantan, in the form of contact pads, and connections or output terminals 8 for transferring the signal of the sensor device 1, made of copper, in the form of contact pads. In particular, the sensor device 1 provides an output voltage Vab on the output terminals 8 thereof, simply indicated also with "a" and "b".

In general, it is known that by powering a resistor having a ohmic value equal to R with a certain electric current I, it dissipates an electric power Pr=R*I$^2$ which turns into heat and causes a rise in temperature, which is higher in a region next to the resistor with respect to a region positioned at a higher distance. In the case of a sensor device 1 being immersed in a fluid, the value of the temperature difference between these two regions also depends on the value of the thermal exchange between the fluid and the sensor itself, in particular on the speed at which the fluid hits the sensor and on the fluid density.

Figure 3A:
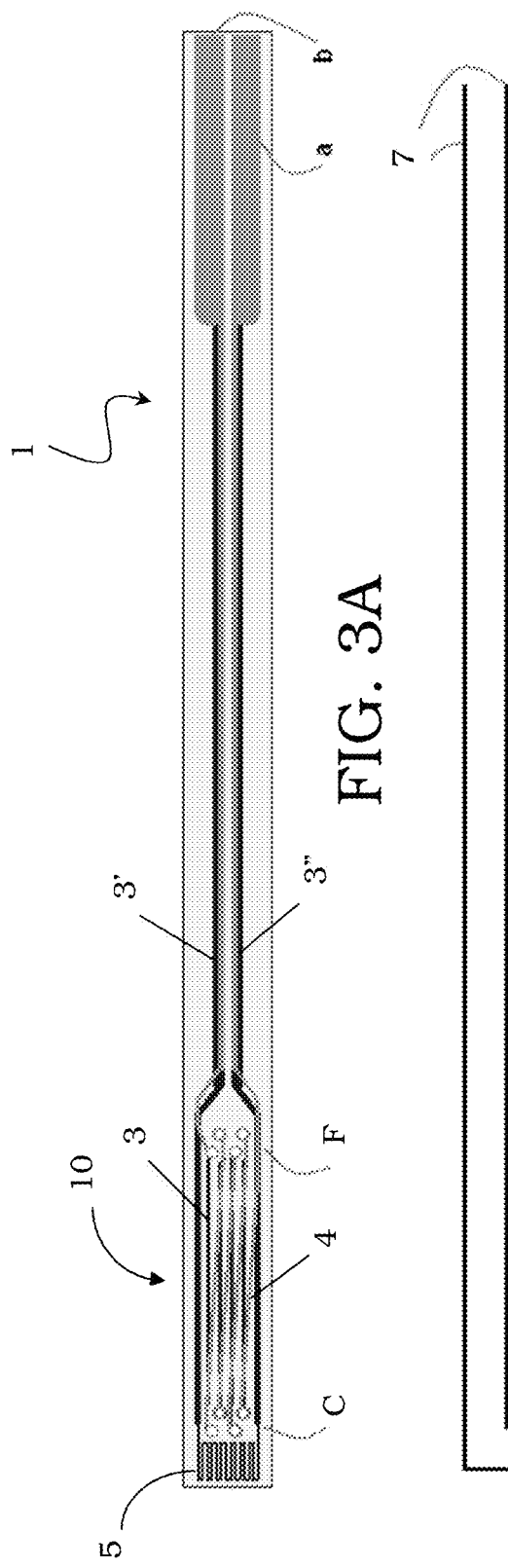
FIGS. 3A and 3B schematically show the sensor device of FIG. 1 in an overall against the light view and according to an electric functional equivalent circuit thereof respectively.

FIG. 3A schematically illustrates the sensor device 1 with the insulating laminated support 2 seen from the copper side 2B and against the light the constantan conductive tracks 3' and 3" connected to the heater. The electric functional equivalent circuit of the sensor device 1 is shown in a simplified form in FIG. 3B.

Figure 3B:
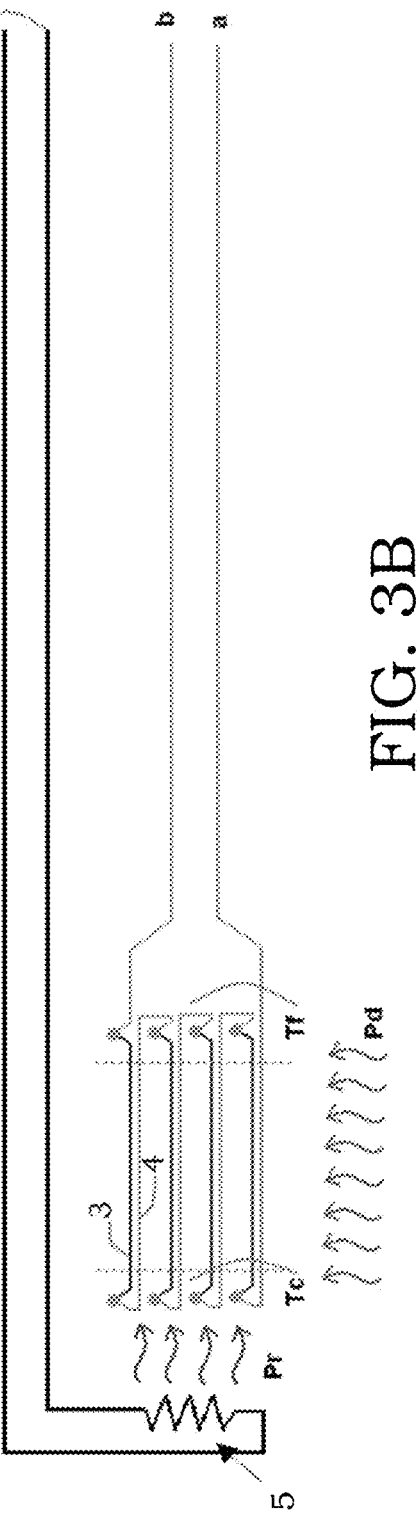

In particular, in this FIG. 3B the thermal exchange with the fluid is represented by means of a certain power Pd comparing with a thermal power Pr of the heating element 5. It is evident that a low speed of the fluid in which the sensor device 1 is immersed involves a low power Pd, and thus the temperature difference created between the two regions in which the hot C and cold F junctions are respectively grouped is the highest, while with high fluid speeds the temperature difference between the region near the heating element 5 and that being far and thus between the hot C and cold F junctions of the thermocouple circuit 10 is lower.

The sensor device 1 comprising the thermocouple circuit 10 thus provides a signal which is proportional to the temperature difference created between the two regions, i.e. between the junctions of the thermocouple circuit 10, this difference depending on the speed of a fluid touching the sensor device 1: it is thus possible to obtain an electric signal being correlated to the speed of this fluid and thus, for the same passage section, correlated to the flow rate thereof.

Similarly to what has just been described for the speed or the flow of a fluid, it is possible to determine the presence/absence of a substance in thermal contact with regions C and F. In particular, if the substance is absent, a low thermal exchange and thus a low power Pd are present. Therefore the temperature difference created between the two regions wherein the hot C and cold F junctions are grouped is the highest. Dually, if the substance is present, and it is thus able to absorb a higher quantity of power Pd, the temperature difference between the region near the heating element 5 and that being far and thus between the hot C and cold F junctions of the thermocouple circuit 10 is lower. In other words, if Pd is the power that the sensor exchanges by thermal contact with the substance, if such a substance is present the power Pd is higher than in the case in which this substance is absent.

The sensor device 1 comprising the thermocouple circuit 10 thus provides a signal which is proportional to the temperature difference created between said two regions, i.e. between the junctions of the thermocouple circuit 10, this difference depending on the presence or absence of the substance in thermal contact with regions C and F of the sensor device 1. It is thus possible to obtain an electric signal being correlated to the presence/absence of the substance in correspondence with regions C and F and thus to the achievement or not of the level corresponding to the position of regions C and F.

More particularly, the value of the output voltage Vab (in microvolts) of the sensor device 1 is given by:

$$Vab = n*S*(Tc-Tf)$$

where n is the number of thermocouples comprised in the thermocouple circuit 10 being series-connected to each other to form a thermopile;

S is the Seebeck coefficient and it depends on the materials chosen to make the thermocouple; in particular, the Seebeck coefficient is the voltage value in microvolts generated in the thermocouple for each Celsius degree of difference between the hot junction and the cold junction; in the case of copper-constantan thermocouple, this coefficient is equal to about 40 microvolts/° C. in the range of temperatures wherein the use of the sensor device is envisaged (this value changing according to the thermoelectric couples being formed: for example for iron-constantan it is equal to about 54); and Tc and Tf are the temperature values of the hot and cold junctions of the thermocouple circuit 10, respectively.

By way of example, in the case of a sensor device 1 comprising a thermocouple circuit 10 composed of four series-connected thermocouples and a heating element 5 powered with a suitable electric current the following results are obtained, in two different temperature difference conditions between the heated and non-heated regions of the sensor device 1, i.e. in two different exchange conditions with the fluid corresponding to two different values of Pd:

1) Tc=45° C.; Tf=25° C. Vab=4*40*(45−25)=3200 microV

2) Tc=35° C.; Tf=25° C. Vab=4*40*(35−25)=1600 microV

It is worth noting that the sensor device 1 can be defined as "asymmetrical" in terms of space, since the heating element 5 and constantan conductive tracks 3 are obtained in one side 2A, while copper conductive tracks 4 are obtained in the other side 2B, and metalized holes 6 forming the junctions C and F of the thermocouple circuit 10 are present through the support.

A sensor device of this type, even if inserted in a metal pipe-like housing tending to uniform heat distribution, is however sensitive to the direction of the thermal flow, i.e. of the fluid touching it.

This peculiar feature is however substantially irrelevant when measuring a level of a fluid and it involves slight differences in the electric response when measuring the flow of a fluid thus suggesting to insert the sensor device 1 according to the invention in a pipe or in a duct preferably with the sensor device 1 surface wherein the heating element 5 is obtained facing the flow, so as to have the highest sensitivity of the sensor device 1 itself.

Instead, a very interesting consequence of this "asymmetry" is used, according to an aspect of the invention, to measure a level of a substance in a container, as schematically shown in FIGS. 4A and 4B. In this case, the sensor device 1 is not immersed in a container 11 comprising a given substance 12, but it is steadily fixed to the wall of the container 11 itself. In view of the above arguments, it is preferable to fix the sensor device 1 on the container 11 on the heating element 5 side, i.e. with the first side 2A being applied onto the container 11. It works also with plastic or glass walls, as long as the thickness is low enough.

By creating a good thermal contact between the wall of the container 11 and the regions of the sensor device 1 defined as the "hot" region and the "cold" region, each one in correspondence with the heated or hot C and non-heated or cold F thermocouple junctions, and powering with an electric current the heating element 5, a temperature difference is created between the two regions and thus an electric signal due to the thermoelectric effect can be detected at the output of the sensor device 1.

Of course, the temperature difference between these two regions, and thus the electric output signal provided by the sensor device 1, is affected by the presence or absence of the substance within the container. If the substance 12 is absent in correspondence with the sensor device 1, as indicated in FIG. 4A, there is a higher temperature difference, while if the substance 12 is present, as indicated in FIG. 4B, a reduction in the temperature difference is obtained since part of the thermal power generated by the heating element 5 passes through the container walls and it is dissipated by the substance 12 itself.

In this way, with the sensor device 1 it is possible to detect the presence of the substance in the region in which the sensor device itself is installed and, indirectly, also to obtain a measuring of the achievement of a certain level of substance 12 in the container 11, though it is not a continuous level measuring. There is nothing to prevent more sensors from being arranged close to each other, at different heights along the wall of the container 11, so to detect in more locations the achievement of a certain level of substance 12 in the container 11, thus obtaining an "almost continuous" level measuring. The level detecting mode performed by the sensor device 1 is very advantageous in several situations, since it is not "invading", i.e. it does not require any modification, such as for example a drilling, of the wall of the container 11 and the immersion of at least one probe therein, thus allowing application costs to be reduced and avoiding particular problems such as for example the presence in the container of a foreign body, contamination, corrosion and also the risk of explosion.

Of course, in order to obtain an easy measurable temperature decrease between the hot and cold regions and thus a change of the electric signal to such an extent that it can be interpreted as a presence of the substance 12 in the region of the container 11 whereto the sensor device 1 is applied, outside the container 11 itself, the thermal features of the substance 12, of the container 11 walls and of the sensor device 1 should be suitable.

In other words, the thermal exchange between the "hot" and "cold" regions of the sensor device 1 should be sufficiently disturbed by the presence or absence of the substance 12 around the region of application of the sensor device 1 itself.

It is worth underlying that the sensor device 1 operates also if the substance 12 comprised in the container 11, or anyway surrounding the sensor device 1 according to the invention, is of the solid and not liquid type, as long as the substance is in the form of powder or granules and with such a density allowing a thermal exchange with the sensor device 1.

In particular, the sensor device 1 indicated in FIGS. 4A and 4B can be steadily fixed to the outer wall of a pipe rather than to the wall of a container.

In this way the sensor device 1 provides an electric signal depending on the thermal exchange between the regions C and F thereof and on the substance contained within the pipe.

It is thus possible to obtain some information in a non-invading way about the condition of the substance within the pipe.

If the pipe is intended to contain a liquid the electric signal at the output of the sensor device 1 allows in particular to understand if the liquid is present or absent or even partially absent, for example due to the presence of gas bubbles.

If the pipe contains a moving fluid the electric signal at the output of the sensor device 1 is correlated to the speed and thus to the fluid flow rate in the pipe.

If the pipe contains instead a high-pressure gas the electric signal at the output of the sensor device 1 allows to understand if gas is present or absent since the thermal exchange between the regions C and F and the gas itself is affected by gas density and thus by gas pressure.

Finally, if the pipe contains solid particles and these have suitable thermal exchange features, the electric signal at the output of the sensor device 1 allows to understand if the particles are present or absent or even partially absent within the Pipe.

According to an embodiment of the invention, the sensor device 1 is made through a multi-layer printed circuit board support 13, as schematically shown in FIGS. 5A and 5B. Elements which structurally and functionally correspond to the sensor device 1 described with reference to FIGS. 1A, 1B and 2 will be given the same reference numbers for simplicity of exposition.

In particular, the multi-layer printed circuit board support 13 comprises two or more stacked supports, equipped of at least an intermediate constantan layer wherein the heating element 5 is to be made inside the sensor device 1.

In the example of FIGS. 5A and 5B, the multi-layer printed circuit board support 13 comprises a first insulating support 13A and a second insulating support 13B, in particular printed circuit board strips, being overlapped to each other and having a corresponding size.

The first insulating support 13A is coated on the upper side (in the local reference of the figures) with a first copper conductive layer 15A wherein copper conductive tracks 14A are obtained. Similarly, the second insulating support 13B is coated on the lower side with a second copper conductive layer 15B wherein copper conductive tracks 14B are obtained.

A third conductive layer or inner layer 15C, in particular a constantan layer, is arranged between the first and second insulating supports 13A and 13B; further constantan conductive tracks 14C are made in this constantan layer.

It is worth noting that the multi-layer configuration being described allows a balanced and further miniaturizable sensor device 1 to be obtained. The heating element 5 in particular is obtained between insulating supports, making constantan tracks having a width even lower than 0.1 mm Heat thus diffuses in a uniform way towards the two upper and lower copper conductive sides. The sensor device 1 is thus particularly useful in those operating conditions in which the sensor insertion position with respect to its axis cannot be exactly foreseen or providing for the sensor device 1 to rotate around its axis with respect to a fluid flow being measured.

According to an aspect of the disclosure, copper conductive tracks 14A and 14B are connected through metalized holes (vias) 6 to constantan conductive tracks 14C, arranged inside the sensor device 1 which is thus equipped with a temperature sensor in the form of a thermopile circuit, always indicated with 10.

It is worth underlying that the thermopile circuit 10 allows a higher signal to be provided with respect to a single thermocouple.

Moreover, thanks to the presence of a heating element 5 not being obtained in a surface layer but rather inside the multi-layer printed circuit board support 13, the sensor device 1 allows a still more uniform response to be obtained with respect to the single insulating laminated support configuration.

Furthermore, the sensor device 1 according to this embodiment requires less heating power for the same response, thus having stronger measuring features. Moreover, since at least three metallic layers are provided (two copper outer layers and one constantan inner layer), connections can be optimized and the sensor device 1 size further reduced.

More particularly, as shown in FIGS. 6A-6C, the multi-layer printed circuit board support, indicated with 13 in FIG. 5B, has outer sides made of copper layers, 15A and 15B, and a constantan inner layer 15C. FIG. 6A shows the sensor device as seen in a plan view from the layer 15A, while FIGS. 6B and 6C respectively show layers 15C and 15B against the light.

The heating element 5 is obtained in the constantan inner layer 15C, connected through a first vias 6A made in the first insulating support 13A and a second vias 6B made in the second insulating support 13B to respective copper conductive tracks, 7A and 7B, wherethrough a power supply current of the heating element 5 itself will flow.

The other copper and constantan conductive tracks, connected to each other to form thermocouples, are connected to two other conductive tracks 8A and 8B positioned on the outer surfaces to collect an electric signal being correlated to the temperature difference between the hot region and the cold region of the thermopile circuit 10 thus obtained.

It is interesting to point out that the path of the tracks obtained on the three copper and constantan conductive surfaces can be so made as to minimize the noises that the sensor device 1 could pick up by electromagnetic coupling due to coil-shaped paths being formed.

Concerning the implementation mode of multi-layer printed circuit boards, a skilled in the art could refer to the printed circuit board implementation techniques, except for the need to provide laminates comprising not only copper layers but also constantan layers.

In this way, a thermal dispersion sensor is obtained, that generates a signal corresponding to the difference of temperature which is created between two zones, one of which is heated and one not. In particular, the measurement of the difference of the temperature between the two zones is obtained by directly reading the signal generated by the sensor of a temperature difference based on the Seebeck thermoelectric effect and formed by one or more thermocouples. This measuring mode has a series of advantages relating to the bulk and the construction of the sensor, as explained in the following.

In case of measure of flow of a fluid, it should be remarked that the heat exchange between the fluid and the sensor according to the disclosure depends not only on the fluid speed but also on the density of the fluid (in particular, on the number of molecules of the fluid involved in the exchange operation). In this way, the signal that is obtained is a measure of the "mass velocity at a point in the flow", that, in case of a gas, could be expressed as $kg/s*m^2$.

As will be clear for a technical expert in the field, this measured value, multiplied by the section of the pipe or the duct in which the sensor device is inserted, after having calculate suitable compensation coefficients due to the distribution of the velocities in the section and other factors (laminar flow, turbulent, distance from the curves, the probe position in the section, etc.), allows to obtain directly the kg/sec of gas that pass through the sensor device, i.e. the mass flow or mass flow rate. In this way, for a same gas, a low speed and a high pressure (high density) and a high speed and low pressure (low density) may generate the same output from the device, since the only result of the measure would correctly be the kg being flown per unit time.

It is underlined that this is an important difference compared to the known volumetric flow meters (for example those with small turbines moved by the flow of gas) as they measure the $m^3/sec$ of gas (volume per unit of time) and, in order to obtain the kg/sec of gas it should be thus necessary to know at least the pressure of the gas and its temperature in order to obtain its density (the meter requiring at least further probes for obtaining these additional parameters of the fluid).

It should be further remarked that the device sensor according to the disclosure would be very useful in many case, wherein is more important to know the mass flow rate rather than the volumetric flow rate. For example, the mass flow rate is to be evaluated in the cases involving energy phenomena; in fact, in these case, in order to evaluate the consumption of gas, for instance involved in a combustion process, or the amount of air entering into an engine, etc., the kg of gas at stake is important, not its volume. Therefore, the proposed device sensor could be inserted into a gas meter.

According to a further aspect of the invention, the sensor device 1 is simplified by using only two wires, as shown in FIGS. 7A-7C. Such a modified sensor device 1 (together with its measuring electronics) can be further miniaturized, more easily connected and more easily manufactured.

In this case, the sensor device 1 comprises an insulating laminated support, indicated with 2 in FIG. 1, equipped with a constantan layer on the one side and with a copper layer on the opposite side, conductive tracks 3 and 4 being made on these layers as shown above. Connection vias completing the thermocouple structure pass through the insulating laminated support, these vias being provided to set an electric connection between the conductive tracks 3 and 4 on the two opposite sides of the insulating laminated support 2. Actually, the example of FIGS. 7A-7C shows two series-connected thermocouples or a two-elements thermopile.

According to an aspect of the invention, the heating element 5 is connected to thermocouples to form only one electric circuit and the heating power supply is alternated in time, to allow the signal coming from thermocouples themselves to be read.

Since the thermocouple ohmic resistance is close to zero ohm or anyway much lower than the heating element's one, during the electric current supplying step all the electric power is concentrated on the resistance composing the heating element 5.

On the contrary, when the electric power supply is interrupted, it is possible to read a voltage signal Vab provided at the thermocouple output. In fact the resistance of the heating element 5 has a value of some dozens or at most hundreds of ohms and this resistance does not affect the reading step of the voltage signal Vab generated by thermocouples.

In particular, a few milliseconds are required to read this voltage signal Vab, while the thermal dynamics involved for the sensor device 1 are of about one second or fraction of second. Therefore, for almost all the working time of the sensor device 1, the heating element 5 is powered, a short interruption at predetermined intervals (for example of 1 millisecond every 0.1 seconds) being enough to read the output voltage signal Vab.

In this case, the heating element 5 and the hot junction C are connected to each other (point PC in FIG. 7A) in correspondence with the hot region, in order to perfectly integrate heating and measuring elements of the sensor device 1.

It is worth noting that the reduction in connection wires is allowed by the electrical integration of the heating element 5 with the hot junction (or junctions) of the thermocouple (or thermocouples) realizing the sensor device 1, indeed.

In its more general aspect, the present disclosure also relates to a method for measuring the flow of a fluid and/or the presence or the level of a substance by using a sensor device 1 as above described and comprising the steps of:

supplying with an electric current the heating element 5 associated to the thermocouple sensor 10 of the sensor device 1 during a first time interval;

interrupting the supplying step of the electric current during a second time interval, shorter than the first time interval and fixed so that, during the second time interval, the temperatures of the hot and cold junctions, C and F, of the thermocouple sensor 10 are substantially unchanged; and detecting during the second time interval a voltage signal provided at the output of the thermocouple sensor 10.

In particular, the voltage signal provided at the output of the sensor 10 is proportional to the temperature difference between the hot and cold junctions, C and F, of the sensor 10 and thus allows the desired measuring of the flow of a fluid and/or of the presence or level of a substance.

It is evident that, if the temperature of the hot and cold junctions C and F changes, in the second time interval related to the detection of the voltage signal provided at the output of the sensor 10, it will be possible to make some adjustments, such as for example an average of the detections performed during this interval, to allow the flow and/or the presence or level to be properly measured.

In particular, the sensor device 1 is connected to a detection circuit 20 in correspondence with its electric connections a and b, as shown in FIG. 8A.

In the example of this figure, the "b" connection is connected to a ground GND and the detection circuit 20 essentially comprises an amplifier A connected, through a switch SW, to the "a" connection and to a current generator Ir respectively.

FIG. 8B represents instead the time intervals T1 during which the switch SW is in a first position, indicated with 1, wherein the heating element 5 is powered with a certain electric power Pr. In time intervals T2, the switch SW is moved into a second position, indicated with 2, wherein the signal Vab of the thermocouple (or thermocouples) is inputted to the amplifier A, at the output of this amplifier A thus providing a voltage Vu depending on the temperature difference Tc-Tf between the hot C and cold F junctions of the thermocouple circuit 10.

As it will be noted, in the diagram of FIG. 8B it has been supposed that temperatures Tc and Tf are gradually approaching, for example after an increase in the dissipative power Pd (as it happens when the sensor device 1 is used as a flow sensor), or after that the sensor has moved from a position in the air to an immersion in a liquid (as it happens when the sensor device 1 is used as a level sensor) and it is thus noted that the voltage Vu in the second interval T2 has a considerably lower value.

The example shown in FIG. 8A is simplified and related to a conceptual scheme which is useful to understand the operation of the sensor device 1. According to an aspect of the invention, the detection circuit 20 comprises in particular a switch SW comprising a series of switches, for example solid-state switches, which can be switched on and off by a suitable microcontroller 21.

Figures 9A, 9B:
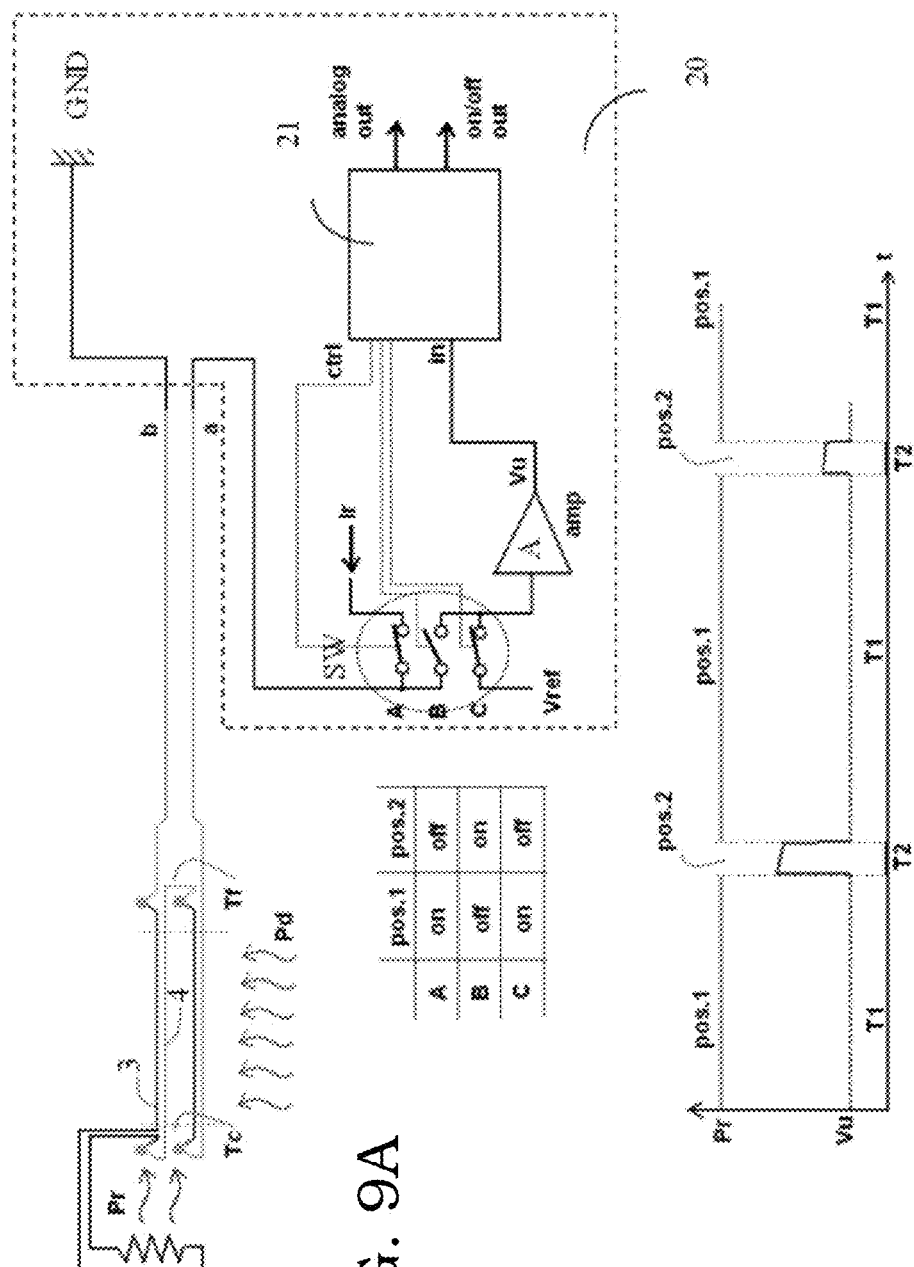
FIGS. 9A and 9B schematically show the functional equivalent circuit of the sensor device of FIGS. 7A-7B associated to a detection circuit according to an alternative embodiment of the invention and a voltage signal as detected respectively.

The example of FIG. 9A shows three switches indicated with A, B and C, which can take each two different configurations or positions, indicated with pos.1 and pos.2, thanks to suitable control signals "ctrl" provided by the microcontroller 21 depending on how the latter has been programmed.

The possible configurations are summarized by way of indication in the table of the figure.

In particular, when the configuration pos.1 is enabled, the sensor device 1 is powered during a certain time interval T1 with a current Ir since the switch A is closed (on).

This current Ir pass through the heating element 5 which dissipates a certain power Pr causing a rise in temperature Tc in the thermocouple junction or junctions close to the heating element 5 itself, i.e. the hot junctions C.

During the same time interval T1 the switch B is open (off) and the switch C is closed (on). In this way a known signal equal to Vref is present at the input of the amplifier A and the output Vu of the amplifier A will have a certain value, indicated with V1, corresponding to the gain of the amplifier A multiplied by Vref.

Afterwards, when the configuration pos.2 is enabled, during a certain time interval T2 the switch A is open (off), the switch B is closed (on) and the switch C is open (off).

In this condition the sensor device 1 generates a voltage Vab being proportional to the temperature difference Tc-Tf between the hot and cold junctions, this voltage Vab being amplified in order to obtain at the output of the amplifier A a voltage Vu with a value V2. This value V2 is equal to the voltage signal Vab provided by the sensor device 1 multiplied by the gain of the amplifier A.

The microcontroller 21, internally equipped in this case with an analog/digital converter, reads through an analog input "in" the voltage Vu values in correspondence with both configurations pos.1 and pos.2.

It is evident that by repeatedly reading in series the two voltage values V1 and V2 and calculating the difference between them, the microcontroller 21 obtains a value representing the amplified difference between the signal Vab provided by the sensor device 1 and the voltage Vref. It is worth underlying that the calculation of the difference between the two voltages corresponding to the two different switch configurations allows the possible amplifier A offsets and drifts to be removed, allowing more economical components and/or very high amplifications to be used without degrading the quality of the signal being measured by the sensor device 1.

By way of example, the amplified signal of the sensor device 1, being linearized and suitably conditioned, could be provided to a pin "analog out" of the microcontroller 21, when it is important to have a continuous signal linked to the flow rate value of the fluid touching the sensor device 1 and/or a digital signal could be provided to a pin "on/off out" of the microcontroller 21 which will be able to take a high or low value depending on whether the fluid flow rate has achieved and/or exceeded a certain threshold or when the sensor device 1 is used to detect the presence of a substance (use as a level sensor).

According to an aspect of the invention, the microcontroller is programmed by a suitable firmware program comprising at least the following steps:

- step 1 with a duration T2 (pos.2 in the table of FIG. 9A) wherein the switches A and C are open, while the switch B is closed; in this step 1, the signal Vab of the sensor device 1 is amplified and a signal of value V2 is obtained at the output of the amplifier A which is stored by the microcontroller 21;
- step 2 with a duration T1 (pos.1 in the table of FIG. 9A) wherein the switches A and C are closed, while the switch B is open; in this step 2, the signal of value V1 is read at the output of the amplifier A which is subtracted from the signal of value V2 stored in the previous step.

In this way, a signal (whose value is the difference between the two values V2-V1) is obtained, which is proportional to the temperature difference between the hot and cold junctions of the sensor device 1 and thus linked to the thermal exchange with the fluid touching it which is not affected by possible offsets and drifts of the amplification circuit.

The difference value being found is then further processed by the program comprised in the microcontroller 21 in order to generate a signal tied to the flow or to the presence or absence of the substance (level).

Figure 10A:
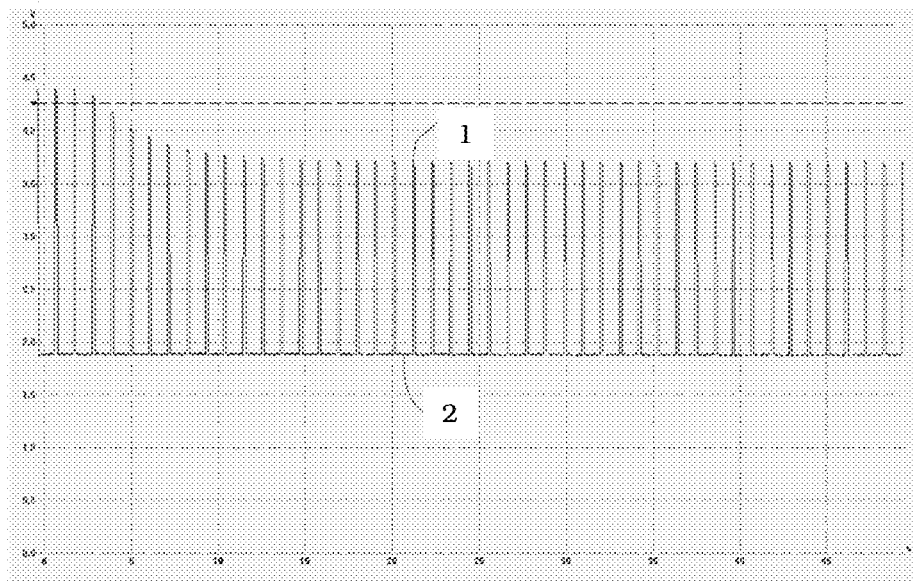
FIGS. 10A and 10B show the trend of the results obtained through experimental tests being performed by the Applicant itself.
Figure 10B:
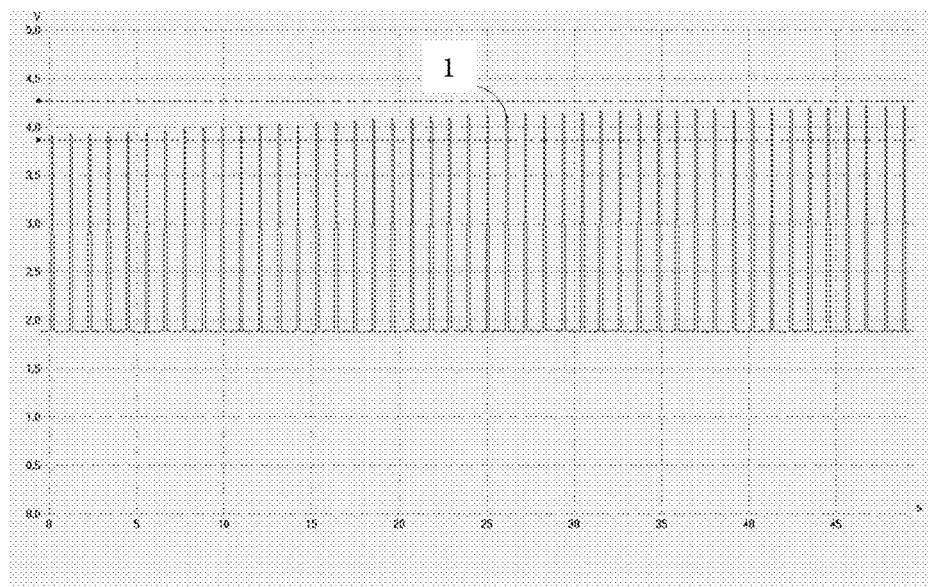

Experimental tests performed by the Applicant itself have led to the results shown in FIGS. 10A and 10B.

In particular, FIG. 10A shows the trend of the output voltage Vu of the amplifier A of the detection circuit 20 in correspondence with the above described steps 1 and 2. It is noted how, while in step 2 the amplifier output Vu (indicated with 2 in the figure) is equal to V1 (about 1.8V), depending on the value of Vref and on the gain of the amplifier being used, when passing from the condition in which the sensor device 1 is in air to the immersion thereof into water, a considerable signal change is obtained in correspondence with step 1 having a duration T2. The amplifier output Vu (indicated with 1 in the figure) which is equal to V2 goes from about 4.4V (sensor device in air) to about 3.7V (sensor device immersed into water).

It is clear that such a considerable change of the output signal Vu can be used to indicate the presence or absence of the liquid, and thus to make a level sensor which will be of the on/off type, i.e. the fluid has achieved or it has not achieved the position of the sensor device 1.

FIG. 10B shows instead the trend of the voltage Vu at the output of the amplifier A in the case of the two-wire sensor device 1 in air. In particular, the initial part of the diagram corresponds to an air flow obtained by approaching the sensor device 1 to a small fan positioned at about 10 cm from the sensor device itself while it rotates at the highest speed. The small fan speed is then gradually reduced up to be set at zero: accordingly, an increase in the voltage value at the amplifier output is noted. The wide change of the output voltage (indicated with 1 in the figure) between 4.1 V (flow max) and 4.4V (flow at zero, i.e. still air) allows a continuous measuring device of the air speed and thus of the flow rate to be set up if the sensor device 1 is placed in a passage having a known section.

In a general form, basically two modes of controlling the heater are possible:

a) by injecting a fixed power in the heater, the output signal of the at least one thermocouple would be checked, such a signal depending on the difference of temperature between the hot and cold junctions; since this signal also depends on the heat exchange, the measure of the flow and/or the level of a fluid or of a substance could be calculated;

b) by injecting in the heater a power amount that serves to maintain a constant difference of temperature between the hot and cold junctions; if there is no heat exchange, this power amount would be minimal, otherwise, if there is heat exchange, this power amount would be higher.

While in the first case the signal to be processed to obtain the flow (or level) is the output signal of the at least one thermocouple, in the second case the signal to be processed is the power amount as supplied to the heater to maintain constant the output signal of the at least one thermocouple, the measure of the output signal being always very important, in this case being kept constant by adjusting the power amount as supplied.

It is also worth noting that the sensor device 1 according to the invention can be placed in a suitable housing, such as for example a metallic pipe or a plastic container, both to protect the elements composing the sensor device 1 and to electrically insulate it from the contact with the substance or the fluid. Of course, also the housing intervenes in the thermal exchange between the regions C and F of the sensor device 1 and the substance or the fluid. Therefore the housing is to be properly sized to avoid excessive losses of sensitivity in correspondence with the changes of the electric output signal of the sensor device 1. In this case, in fact, it will be the housing comprising the sensor device 1 to be immersed in the fluid or in the substance whose flow and/or presence or level is to be measured. In alternative, this housing comprising the sensor device 1 can be steadily fixed to the outer wall of a container and/or pipe comprising the fluid and/or the substance being measured.

In substance, the sensor device 1 according to the invention allows a flow and/or level sensor to be made, which is based on the Seebeck thermoelectric effect, highly miniaturizable at low cost, with a reliable and accurate response.

The sensor is actually sensitive to the thermal exchange with the surrounding environment, and thus with the fluid wherein it is immersed or with the substance with which it is in thermal contact. In particular, this exchange in the case of a fluid depends on its speed and also on its density.

Therefore, if the fluid has the same density and its speed changes, a measure being correlated to the speed, and thus to the flow rate or flow of the fluid is possible, when passing through a constant section. If instead the fluid has not the same density, or if the fluid is of a different type, passing for example from air to water or to other liquids or even from air to solid, it is possible to make a sensor measuring the level or better the presence/absence of a substance. More particularly it is underlined that the sensor device 1 comprising a sensor 10 which is based on the Seebeck thermoelectric effect with a heating element made in the support of the sensor device itself, when compared to known devices, is:

- more economical since the heating element 5 is directly obtained in the support through the printed circuit board technology, with no need to be bought as a separate component;
- more accurate and repetitive in the electric response since the heating element is obtained in the support of the sensor device in a well-defined position, with no uncertainties and positioning and/or thermal contact tolerances;

more rapid in the response since it has a mass and thus a thermal inertia being lower near the hot junction thereof;

more effective since it is possible to bring the heating element closer to the hot junction, subsequently obtaining a desired signal by using a lower power provided by the heating element itself;

smaller and more miniaturizable since the heating element dimension as a separate element is removed, overcoming also the need to find a place for the related contact pads;

simpler to connect when the heating element and the hot junction are integrated with each other, connecting in series the resistor and the thermocouple, making in particular a two-wire device.

In substance, the sensor device made according to the invention is very easy to manufacture, not requiring in particular successive assembling steps of the heating element as in known devices, it has a low cost and a reduced dimension with respect to known devices as well as a more reproducible manufacturing.

In the multi-layer embodiment, as shown for example in FIGS. 5A-5B and 6A-6C, the sensor device according to the disclosure further has a reduction in consumptions and a more homogeneous behavior, with the possibility to use ground planes or particular arrangements of the conductive tracks to reduce noises. This multi-layer sensor device also provides two surfaces for assembling for example SMT (acronym for: "Surface Mount Technology") electronic components for signal conditioning or first amplification, allowing, if necessary, a very compact sensor to be made, which is already equipped with an onboard electronics for signal amplification and conditioning and possibly also for measure output generation.

Finally, the two-wire embodiment shown in FIGS. 7A-7C allows a particularly compact sensor device to be obtained, thanks to the reduction in connection wires.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A sensor device for measuring the flow of a fluid and/or the presence or level of a substance comprising:
    a support being equipped with a sensor of a temperature difference based on the Seebeck thermoelectric effect and being a multi-layer printed circuit board support which includes:
    at least one first insulating support,
    a second insulating support,
    an inner conductive layer of a first conductive material separating the first and second insulating supports,
    the first and second insulating supports having their respective exposed surfaces coated with a first conductive layer of a second conductive material and with a second conductive layer of the second conductive material,
    first conductive tracks which are obtained in the first and second conductive layers, and
    second conductive tracks which are realized in the inner conductive layer
    through and metalized holes being provided in the first and second support elements to connect the first conductive tracks with the second conductive tracks, thus creating at least one thermocouple of the sensor,
    a heating element being also associated to the sensor and being internally realized in the multi-layer printed circuit board support in the inner conductive layer of the first conductive material.

2. The sensor device of claim 1, wherein the first and second insulating supports are insulating supports made of a laminated material as used in the printed circuit board technology.

3. The sensor device of claim 2, wherein the first conductive material is constantan and the second conductive material is copper.

4. The sensor device of claim 1, wherein the heating element is directly made of and embedded in the inner conductive layer using the printed circuit board technology.

5. The sensor device of claim 1, further comprising:
    power connections to the heating element, which are made in the first and second conductive layers, in the form of contact pads, and
    output terminals for transferring an output signal of the sensor device, which are realized in the first and second conductive layers, in the form of contact pads.

6. The sensor device of claim 1, further comprising:
    at least first and second through and metalized holes which are made in the first and second insulating supports, respectively, for connecting the heating element to respective conductors which are made in the first and second conductive layers, respectively, and to provide a power supply current to the heating element.

7. The sensor device of claim 1, further comprising:
    respective output terminals which are made in the first and second conductive layers, respectively, for the transmission of an output signal of the sensor.

8. The sensor device of claim 1, wherein the heating element is electrically connected to the at least one thermocouple of the sensor, preferably to the hot junction of the at least one thermocouple.

9. The sensor device of claim 1, further comprising:
    SMT electronic components provided on at least one of its surfaces for realizing onboard electronics for signal amplification and conditioning.

10. The sensor device of claim 1, wherein the heating element is realized close to the at least one thermocouple of the sensor, preferably to the hot junction of the at least one thermocouple.

11. The sensor device of claim 1, further comprising:
    a plurality of sensors arranged close to each other.

12. Use of a sensor device for measuring the flow of a fluid and/or the presence or level of a substance which comprises:
    a support being equipped with a sensor of a temperature difference based on the Seebeck thermoelectric effect and being a multi-layer printed circuit board support which includes:
    at least one first insulating support
    a second insulating support,
    an inner conductive layer of a first conductive material separating the first and second insulating supports
    the first and second insulating supports having their respective exposed surfaces coated with a first conductive layer of a second conductive material and with a second conductive layer of the second conductive material,
    first conductive tracks which are obtained in the first and second conductive layers, and
    second conductive tracks which are realized in the inner conductive layer
    through and metalized holes being provided in the first and second support elements to connect the first conductive tracks with the second conductive tracks, thus creating at least one thermocouple of said sensor, a heating element being also associated to the sensor and being internally realized in the multi-layer printed circuit board support in the inner conductive layer of the first conductive material as an external sensor being fixed in a stable manner to a container and/or to a pipe for measuring the flow of a fluid and/or the presence or level of a substance in the container and/or pipe.

13. Use of a sensor device for measuring the flow of a fluid and/or the presence or level of a substance comprising:

a support being equipped with a sensor of a temperature difference based on the Seebeck thermoelectric effect and being a multi-layer printed circuit board support which includes:

at least one first insulating support a second insulating support, an inner conductive layer of a first conductive material separating the first and second insulating supports the first and second insulating supports having their respective exposed surfaces coated with a first conductive layer of a second conductive material and with a second conductive layer of the second conductive material, first conductive tracks which are obtained in the first and second conductive layers, and second conductive tracks which are realized in the inner conductive layer through and metalized holes being provided in the first and second support elements to connect the first conductive tracks with the second conductive tracks, thus creating at least one thermocouple of said sensor, a heating element being also associated to the sensor and being internally realized in the multi-layer printed circuit board support in the inner conductive layer of the first conductive material and comprising a plurality of sensors arranged close to each other as an external sensor being fixed in a stable manner to a container and/or to a pipe to detect in more locations the achievement of a certain level of a substance in the container and/or pipe, thus obtaining an almost continuous level measuring.

14. A method for measuring the flow of a fluid and/or the presence or level of a substance wherein it uses a sensor device which comprises:

a support being equipped with a sensor of a temperature difference based on the Seebeck thermoelectric effect and being a multi-layer printed circuit board support which includes:

at least one first insulating support a second insulating support, an inner conductive layer of a first conductive material separating the first and second insulating supports the first and second insulating supports and having their respective exposed surfaces coated with a first conductive layer of a second conductive material and with a second conductive layer of the second conductive material, first conductive tracks which are obtained in the first and second conductive layers, and second conductive tracks which are realized in the inner conductive layer through and metalized holes being provided in the first and second support elements to connect the first conductive tracks with the second conductive tracks, thus creating at least one thermocouple of said sensor, a heating element being also associated to the sensor and being internally realized in the multi-layer printed circuit board support in the inner conductive layer of the first conductive material the method comprising the steps of:

supplying with an electric current the heating element associated to the sensor of the sensor device during a first time interval;

interrupting the supplying step of the electric current for a second time interval, which is shorter than the first time interval and fixed so as the temperatures of the hot and cold junctions of the sensor are substantially unchanged during the second time interval, and detecting a voltage signal being provided at the output of the sensor during the second time interval, the voltage signal being provided at the output of the sensor being proportional to the difference of the temperatures of the hot and cold junctions of the sensor and thus allowing the measuring of the flow of a fluid and/or of the presence or level of a substance.

* * * * *